United States Patent [19]

Beck et al.

[11] 4,012,388
[45] Mar. 15, 1977

[54] HERBICIDAL 4-PYRIMIDINONES AND PYRIMIDINETHIONES

[75] Inventors: James Richard Beck; Robert Peter Gajewski, both of Indianapolis, Ind.

[73] Assignee: Eli Lilly and Company, Indianapolis, Ind.

[22] Filed: Dec. 11, 1975

[21] Appl. No.: 639,526

[52] U.S. Cl. .............................. 260/251 R; 71/92; 260/558 A
[51] Int. Cl.$^2$ ..................................... C07D 239/22
[58] Field of Search ............................... 260/251 R

[56] References Cited

UNITED STATES PATENTS 3,772,288  11/1973  Hartmann et al. ............. 260/251 R
3,823,135  7/1974  Pilgram et al. ................ 260/251 R

FOREIGN PATENTS OR APPLICATIONS 820,869  4/1975  Belgium ........................ 260/251 R

OTHER PUBLICATIONS

J. Chem. Soc. 347–351 (1945).
Herbicide Handbook, 65–69 & 390–393.

Primary Examiner—Lewis Gotts
Assistant Examiner—D. R. Phillips
Attorney, Agent, or Firm—Joseph A. Jones; Everet F. Smith

[57] ABSTRACT

A class of new 4-pyrimidinones and thiones have a small alkyl group at the 1-position and a substituted phenyl group at the 5-position. The compounds are herbicides.

6 Claims, No Drawings

HERBICIDAL 4-PYRIMIDINONES AND PYRIMIDINETHIONES

BACKGROUND OF THE INVENTION

Herbicides are in wide use in all types of agriculture at the present time. Agricultural research has established that the maximization of crop yields and economic return demands the use of appropriate herbicides to eliminate or at least reduce the competition of weeds for soil nutrients, water and sunlight. Many classes of herbicides are now in use. The great number of different crops which are grown economically, the wide variation in soil textures, and the extreme span of climatic conditions in which agriculture is pursued demand a wide range of herbicides of different characteristics. Agricultural chemical researchers continue to investigate possible new herbicides in the hope of finding compounds which have more advantageous properties than their predecessors.

Some pyrimidinone herbicides have been disclosed in the agricultural chemical art, such as the 6-alkyl-2,5-dihalo-3-phenyl-4-pyrimidinones of U.S. Pat. No. 3,823,135 Earlier workers have also found herbicides among the pyridazinones, for example, U.S. Pat. No. 3,644,355. A compound much like those of this invention, but lacking the substituent on the phenyl ring, has been disclosed in the chemical literature. Davies et al., A Novel Pyrimidine Synthesis, J. Chem. Soc. 347–51 (1945). This compound, however, has extremely low herbicidal activity.

SUMMARY

This invention provides to the agricultural chemical art new herbicidal compounds of the formula

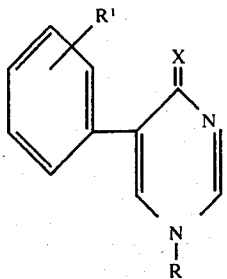

wherein
R represents $C_1$–$C_3$ alkyl;
$R^1$ represents bromo, chloro or trifluoromethyl;
X represents oxygen or sulfur.

The invention also provides new herbicidal methods which make use of the compounds, and herbicidal compositions with which the methods are carried out.

DESCRIPTION OF THE PREFERRED EMBODIMENT

In the formula above, the term $C_1$–$C_3$ alkyl refers to methyl, ethyl, propyl and isopropyl.

While the above generic formula is believed to define the compounds of this invention will complete clarity, a group of typical compounds of the invention will be presented to assure that agricultural chemists understand the invention. The compounds below are not intended to delineate the bounds of the invention.

1-ethyl-5-(2-chlorophenyl)-4(1H)-pyrimidinone
5-(3-chlorophenyl)-1-propyl-4(1H)-pyrimidinone
1-methyl-5-(2-bromophenyl)-4(1H)-pyrimidinethione
1-isopropyl-5-(α,α,α-trifluoro-o-tolyl)-4(1H)-pyrimidinone
1-ethyl-5-(4-bromophenyl)-4(1H)-pyrimidinethione
5-(3-chlorophenyl)-1-propyl-4(1H)-pyrimidinethione
1-methyl-5-(α,α,α-trifluoro-p-tolyl)-4(1H)-pyrimidinethione Earlier workers have made pyrimidinones by relatively long and difficult processes. For example, Davies, cited above, used a process beginning with the reaction of phenylacetonitrile and formamide at very high temperature in the presence of ammonia gas. The product was 4-amino-5-phenylpyrimidine, which was reacted with methyl sulfate to add the 1-methyl substituent, and was then hydrolyzed with strong acid to produce 1-methyl-5-phenyl-4-pyrimidinone. The same compound was made in extremely low yield by Brown et al., Pyrimidine Reactions, J. Chem. Soc. 214–19 (1970), by the thermal rearrangement of 4-methoxy-5-phenylpyrimidine in the presence of triethylamine.

The preferred synthesis of the present compounds proceeds through an intermediate (I) shown below.

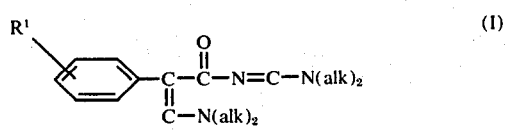

wherein alk represents ethyl or methyl. Similar compounds were shown by Bredereck et al., Chem. Ber. 104, 2709–26 (1971), who made the compounds by the reaction of phenylacetamide with dimethylformamide di(t-butyl) acetal.

The intermediate (I) is preferably formed from an appropriately-substituted phenylacetamide by reaction with di(alk)formamide di(alk) acetal in dimethylformamide. Reaction at about 80°–130° C., and preferably at 100°–120° C., for times in the range of from 1 to 8 hours in an open flask forms the intermediate in good yield.

The intermediate (I) is then reacted with an amine of the formula $RNH_2$ or a combination of $RNH_2$ and a hydrohalide salt thereof, in a solvent, of which lower alkanols, especially methanol, are preferred. The hydrohalide salts include the hydrochlorides, hydrobromides, hydrofluorides and hydroiodides. Other solvents, such as dimethylsulfoxide, dimethylformamide, tetrahydrofuran and the like can also be used. Room temperature is preferred, but temperatures from about 0° C. to about 100° C. can be used.

The pyrimidinethiones of this invention are easily prepared by the reaction of the corresponding pyrimidinone with $P_2S_5$ in pyridine.

The $R^1$ substituents are provided by corresponding substituents on the starting phenylacetamide. All of the starting compounds are readily obtainable.

A few typical preparative examples will be shown for the further assistance of those who wish to obtain the compounds. All of the products of the examples were identified by nuclear magnetic resonance analysis and elemental analysis.

EXAMPLE 1

1-methyl-5-(4-chlorophenyl)-4(1H)-pyrimidinone

A 4.2 g. portion of 4-chlorophenylacetamide was mixed with 6 g. of dimethylformamide dimethyl acetal in 50 ml. of dimethylformamide. The mixture was stirred at 110° C. for about 6 hours in an open flask and was then allowed to cool to room temperature. The reaction mixture was poured over ice, and the precipitated product was separated by filtration and recrystallized from benzene-hexane. The purified intermediate, p-chloro-$\beta$-dimethylamino-N-[(dimethylamino)methylene]atropamide, m.p. 155°–156° C., was obtained in a yield of 2 g.

A 1.2 g. portion of the above intermediate was dissolved in 75 ml. of methanol and 3 g. of methylamine hydrochloride was added. The mixture was stirred at reflux temperature while methylamine was bubbled in. After 1 hour, the mixture was evaporated to dryness, and the residue was taken up in hot ethyl acetate, which was then evaporated to 1/5 of its volume. The product spontaneously crystallized and was separated by filtration. The solids were dissolved in 100 ml. of chloroform, 1 cc. of 1N sodium hydroxide was added, and the solution was stirred for 15 minutes and dried over sodium bicarbonate. The chloroform was evaporated under vacuum, and the product was recrystallized from hot benzene to obtain 0.6 g. of 1-methyl-5-(4-chlorophenyl)-4(1H)-pyrimidinone, m.p. 220°–221° C.

|   | Theoretical | Found |
|---|---|---|
| C | 59.88% | 59.60% |
| H | 4.11 | 3.96 |
| N | 12.70 | 12.73 |

EXAMPLE 2

1-methyl-5-($\alpha,\alpha,\alpha$-trifluoro-m-tolyl)-4(1H)-pyrimidinone

A 2 g. portion of ($\alpha,\alpha,\alpha$-trifluoro-m-tolyl)acetamide was reacted with 1.2 g. of dimethylformamide dimethyl acetal as described in Example 1 to produce 2.7 g. of m-trifluoromethyl-$\beta$-dimethylamino-N-[(dimethylamino)methylene]-atropamide. A 2 g. portion of the atropamide was dissolved in 30 ml. of dimethylsulfoxide, 0.3 g. of methylamine hydrochloride was added, and the mixture was stirred at 90° C. for one hour while methylamine was bubbled through the liquid. The reaction mixture was then poured over ice and the aqueous mixture was extracted with chloroform. The solvent layer was evaporated to dryness and the residue was recrystallized from isopropyl ether to produce 0.75 g. of 1-methyl-5-($\alpha,\alpha,\alpha$-trifluoro-m-tolyl)-4(1H)-pyrimidinone, m.p. 155°–156° C.

|   | Theoretical | Found |
|---|---|---|
| C | 56.70% | 56.49% |
| H | 3.57 | 3.66 |
| N | 11.02 | 11.02 |

EXAMPLE 3

1-methyl-5-(3-chlorophenyl)-4(1H)-pyrimidinone

Using the procedure of Example 1, 4.2 g. of 3-chlorophenylacetamide and 6 g. of dimethylformamide dimethyl acetal yielded 5 g. of the corresponding atropamide, m.p. 116°–117° C. A 1.5 g. portion of the atropamide was reacted with methylamine in methanol to produce 0.7 g. of 1-methyl-5-(3-chlorophenyl)-4(1H)-pyrimidinone, m.p. 213° C.

|   | Theoretical | Found |
|---|---|---|
| C | 59.88% | 60.07% |
| H | 4.11 | 4.05 |
| N | 12.70 | 12.71 |

EXAMPLE 4

1-ethyl-5-($\alpha,\alpha,\alpha$-trifluoro-m-tolyl)-4(1H)-pyrimidinone

Two g. of the intermediate atropamide of Example 2 was reacted with 1 cc. of 20 percent aqueous ethylamine in 20 ml. of methanol. The reaction mixture was stirred at reflux temperature for 6 hours and evaporated to dryness, and the residue was recrystallized from ethyl acetatehexane. The product was 1.3 g. of 1-ethyl-5-($\alpha,\alpha,\alpha$-trifluoro-m-tolyl)-4(1H)-pyrimidinone, m.p. 172°–173° C.

|   | Theoretical | Found |
|---|---|---|
| C | 58.21% | 58.29% |
| H | 4.13 | 3.96 |
| N | 10.44 | 10.48 |

EXAMPLE 5

1-methyl-5-(3-bromophenyl)-4(1H)-pyrimidinone

A 15 g. portion of 3-bromophenylacetamide was reacted with 16.7 g. of dimethylformamide dimethyl acetal as described in Example 1 to produce 18 g. of the corresponding atropamide, m.p. 120°–121° C. A 3.2 g. portion of the atropamide was reacted with methylamine in methanol to produce 1.65 g. of 1-methyl-5-(3-bromophenyl)-4(1H)-pyrimidinone, m.p. 218°–219° C.

|   | Theoretical | Found |
|---|---|---|
| C | 49.84% | 49.56% |
| H | 3.42 | 3.62 |
| N | 10.57 | 10.53 |

EXAMPLE 6

1-methyl-5-($\alpha,\alpha,\alpha$-trifluoro-m-tolyl)-4(1H)-pyrimidinethione

A 2.2 g. portion of the product of Example 2 was dissolved in 25 ml. of pyridine and 2.2 g. of $P_2S_5$ was added. The reaction mixture was stirred at reflux temperature for 4 hours, and was then poured over ice. The aqueous mixture was filtered and the solids were recrystallized from ethanol to produce 1.5 g. of 1-methyl- 5-($\alpha,\alpha,\alpha$-trifluoro-m-tolyl)-4(1H)-pyrimidinethione, m.p. 197°–200° C.

|   | Theoretical | Found |
|---|---|---|
| C | 53.33% | 53.20% |
| H | 3.36 | 3.11 |
| N | 10.36 | 10.27 |

The compounds described above have been tested in a number of herbicidal test systems to determine the range of their herbicidal efficacy. The results produced by the compounds in the representative tests reported below are exemplary of the activity of the compounds.

Compound application rates are expressed in kilograms of the compound per hectare of land (kg./ha.) throughout this document.

Blank spaces in the tables below indicate that the compound was not tested against the named species. In the tests below, plants were rated on a 1–5 scale, on which 1 indicates normal plants and 5 indicates dead plants or no emergence. The compounds are identified by their example numbers.

TEST 1

Broad Spectrum Greenhouse Test

Square plastic pots were filled with a sandy sterilized greenhouse soil and were planted to seeds of tomato, large crabgrass and pigweed. Each pot was individually fertilized.

Test compounds were applied postemergence to some pots and preemergence to others. Postemergence applications of the compounds were sprayed over the emerged plants about 12 days after the seeds were planted. Preemergence applications were sprayed on the soil the day after the seeds were planted.

Each test compound was dissolved in 1:1 acetone: ethanol at the rate of 2 g. per 100 ml. The solution also contained about 2 g. per 100 ml. of an anionic-nonionic surfactant blend. One ml. of the solution was diluted to 4 ml. with deionized water, and 1½ ml. of the resulting solution was applied to each pot, resulting in an application rate of 16.8 kg./ha. of test compound.

After the compounds were applied, the pots were moved to the greenhouse, watered as necessary, and observed and rated about 10–13 days after application of the compounds. Untreated control plants were used as standards in every test.

The table below reports results of testing typical compounds of the invention.

| Compound of Example No. | Preemergence | | | Postemergence | | |
|---|---|---|---|---|---|---|
| | Tomato | Large Crabgrass | Pigweed | Tomato | Large Crabgrass | Pigweed |
| 2 | 5 | 5 | 5 | 4 | 4 | 4 |
| 3 | 4 | 4 | 5 | 4 | 3 | 5 |
| 4 | 5 | 5 | 5 | 5 | 4 | 4 |
| 5 | 4 | 4 | 5 | 5 | 4 | 5 |
| 6 | 5 | 5 | 5 | 5 | 4 | 4 |

TEST 2

Multi-Species Greenhouse Test

The test was conducted in general like the test above. The seeds were planted in flat metal trays, rather than in pots. The compounds were formulated according to the procedure above, except that about 6 g./100 ml. of the compound was dissolved in the surfactant-containing solvent, and the organic solution was diluted with appropriate amounts of water before application to the trays. The compounds were applied at various rates which are indicated in the table below and the results of testing against the species named below are as follows.

| Compound of Example No. | Rate of Appln. kg./ha. | Corn | Cotton | Soybean | Wheat | Alfalfa | Sugar Beet | Rice | Cucumber | Tomato | Barnyard Grass |
|---|---|---|---|---|---|---|---|---|---|---|---|
| 1 | 9.0 | 1 | | | | | | | | | |
| 2 | 9.0 | 4 | | | | | | | | | |
|   | 2.2 | 2 | 1 | 4 | 3 | 5 | 5 | 2 | 5 | 3 | 5 |
|   | 0.56 | 1 | 1 | 2 | 2 | 5 | 4 | 1 | 2 | 2 | 2 |
| 3 | 9.0 | 3 | | | | | | | | | |
|   | 4.5 | 2 | 1 | 3 | 3 | 5 | 5 | 2 | 4 | 2 | 3 |
|   | 2.2 | 1 | 1 | 2 | 2 | 3 | 3 | 1 | 3 | 1 | 2 |
| 4 | 9.0 | 4 | | | | | | | | | |
|   | 2.2 | 1 | 1 | 3 | 2 | 5 | 5 | 1 | 3 | 2 | 3 |
| 5 | 9.0 | 3 | | | | | | | | | |
|   | 2.2 | 2 | 1 | 1 | 1 | 2 | 4 | 1 | 3 | 2 | |
| 6 | 9.0 | 4 | | | | | | | | | |
|   | 2.2 | 1 | 1 | 1 | 2 | 2 | 4 | 1 | 3 | 2 | 2 |

| Compound of Example No. | Rate of Appln. kg./ha. | Lambsquarter | Large Crabgrass | Mustard | Pigweed | Foxtail | Wild Oat | Velvetleaf | Jimsonweed | Morningglory | Zinnia |
|---|---|---|---|---|---|---|---|---|---|---|---|
| 1 | 9.0 | | 2 | | 3 | 2 | | 1 | | 2 | 2 |
| 2 | 9.0 | | 5 | | 5 | 5 | | 5 | | 5 | 5 |
|   | 2.2 | 5 | 5 | 5 | 4 | 5 | 2 | 5 | 4 | 5 | 5 |
|   | 0.56 | 3 | 3 | 2 | 3 | 2 | 1 | 3 | 2 | 2 | 2 |

-continued

| | | | | | Preemergence | | | | | |
|---|---|---|---|---|---|---|---|---|---|---|
| 3 | 9.0 | | 5 | | 5 | 4 | | 5 | | 5 | 4 |
| | 4.5 | 4 | 4 | 3 | 3 | 4 | 1 | 4 | 3 | 4 | 4 |
| | 2.2 | 4 | 4 | 2 | 2 | 3 | 1 | 2 | 2 | 2 | 3 |
| 4 | 9.0 | | 5 | | 5 | 5 | | 5 | | 5 | 5 |
| | 2.2 | 4 | 4 | 3 | 4 | 3 | 1 | 4 | 3 | 4 | 3 |
| 5 | 9.0 | | 5 | | 5 | 4 | | 5 | | 4 | 5 |
| | 2.2 | 2 | 3 | 2 | 2 | 1 | 1 | 3 | 2 | 2 | 2 |
| 6 | 9.0 | | 5 | | 5 | 5 | | 5 | | 5 | 5 |
| | 2.2 | 3 | 4 | 2 | 4 | 2 | 1 | 3 | 3 | 2 | 2 |

| Compound of Example No. | Rate of Appln. kg./ha. | Postemergence | | | | | | |
|---|---|---|---|---|---|---|---|---|
| | | Corn | Large Crabgrass | Pigweed | Foxtail | Velvet-leaf | Morning-glory | Zinnia |
| 1 | 9.0 | 2 | 1 | 2 | 1 | 1 | 2 | 1 |
| 2 | 9.0 | 3 | 3 | 2 | 2 | 2 | 2 | 2 |
| 3 | 9.0 | 2 | 2 | 2 | 2 | 2 | 2 | 2 |
| 4 | 9.0 | 3 | 4 | 3 | 3 | 3 | 3 | 3 |
| 5 | 9.0 | 3 | 3 | 3 | 2 | 3 | 2 | 3 |
| 6 | 9.0 | 3 | 3 | 3 | 3 | 3 | 3 | 3 |

TEST 3

Resistant Weed Test

Typical compounds were evaluated in a test system which determined their ability to reduce the vigor of weeds which are resistant to many herbicides. The compounds were formulated and dispersed, and the dispersions were applied, as described in Test 1 above. The application rate was 9.0 kg./ha. in all of the tests reported here.

| Compound of Example No. | Preemergence | | | | Postemergence |
|---|---|---|---|---|---|
| | Yellow Nutsedge | Night-shade | Sicklepod | Rag-weed | Yellow Nutsedge |
| 1 | 1 | 2 | 2 | 3* | 1 |
| 2 | 4 | 5 | 5 | 5 | 3 |
| 3 | 2 | 4 | 5 | 4 | 2 |
| 4 | 1 | 5 | 5 | 5 | 2 |
| 5 | 2 | 4 | 5 | 4 | 1 |
| 6 | 2 | 4 | 5 | 4 | 2 |

*Tested against prickly sida

The broad-spectrum activity of the compounds of this invention is clearly illustrated by the above examples. The test results point up the efficacy of the compounds against annual grasses, the relatively easily-controlled broadleaves such as pigweed, and the more resistant broadleaves such as nightshades. Plant scientists will recognize that the exemplified activity of the compounds shows that the compounds are broadly effective against unwanted herbaceous plants, which will be referred to as weeds, for the sake of brevity.

As the above test results demonstrate, the compounds are used to reduce the vigor of weeds by contacting them with an herbicidally-effective amount of one of the compounds described above. The term "reduce the vigor of" is used to refer to both killing and injuring the weed which is contacted with one of the compounds. In some instances, as is clear from the test results, the whole population of the contacted weed is killed. In other instances, part of the weeds are killed and part of them are injured, and in still other instances, none of the weeds are killed but are merely injured by application of the compound. It will be understood that reducing the vigor of the weed population by injuring part of them is beneficial, even though part of the population survives application of the compound. The weeds, the vigor of which has been reduced, are unusually susceptible to the stresses, such as disease, drought, lack of nutrients and so forth, which normally afflict plants.

Thus, the treated weeds, even though they survive application of the compound, are likely to expire due to stress of the environment. Further, if the treated weeds are growing in cropland, the crop, growing normally, tends to shade out the treated weeds of reduced vigor. The crop, therefore, has a great advantage over the treated weeds in the competition for nutrients and sunlight. Still further, when the treated weeds are growing in fallow land, or industrial property which is desired to be bare, the reduction in their vigor necessarily tends to minimize the treated weeds' consumption of water and nutrients, and also minimizes the fire hazard and nuisance which the weeds present.

The compounds are herbicidally effective when applied both preemergence and postemergence. Thus, they can be used both by direct contact of the compounds with emerged weeds, and by applying the compounds to the soil, where they come into contact with germinating and emerging weeds. Preemergence application of the compounds, wherein the germinating and emerging weeds are contacted with the compound through soil application, is preferred.

Accordingly, an important embodiment of this invention is a method of reducing the vigor of weeds which comprises contacting the weeds with an herbicidally-effective amount of a compound of the invention. The term herbicidally-effective amount refers to an amount which will reduce the vigor of the treated weed. In the context of this invention, weed seeds, which are contacted with the compounds by application of the compounds to the soil, are regarded as weeds.

Amounts of herbicides are measured in terms of the weight of herbicide applied per unit area, in kilograms per hectare (kg./ha.), usually called the application rate. The best application rate of a given compound of the invention for the control of a given weed varies, of course, depending upon the climate, soil texture, water and organic matter contents of the soil and other factors known to those skilled in plant science. It will be found, however, that the optimum application rate is usually in the range from about 1.0 to about 20 kg./ha.

It is not implied, of course, that all compounds of this invention are effective against all weeds at all rates. Some compounds are more effective against some types of weeds, other compounds are more effective against other types. All of the compounds, however, are effective against at least some weeds. It is within the ordinary skill of a plant scientist to ascertain the weeds which are most advantageously controlled with the various compounds, and the best application rate for the particular use.

The preferred compounds of this invention are 1-methyl-5-($\alpha,\alpha,\alpha$-trifluoro-m-tolyl)-4(1H)-pyrimidinone, 1-methyl-5-(3-chlorophenyl)-4(1H)-pyrimidinone, 1-ethyl-5-($\alpha,\alpha,\alpha$-trifluoro-m-tolyl)-4(1H)-pyrimidinone, 1-methyl-5-(3-bromophenyl)-4(1H)-pyrimidinone, and 1-methyl-5-($\alpha,\alpha,\alpha$-trifluoro-m-tolyl)-4(1H)-pyrimidinethione.

The compounds are applied to the soil or to emerged weeds in the manners usual in agriculture. It is best to apply the compounds in the form of the herbicidal compositions which are important embodiments of the present invention. They may be applied to the soil in the form of either water-dispersed or granular compositions, the preparation of which will be discussed below. Usually, water-dispersed compositions will be used for the application of the compounds to emerged weeds. The compositions are applied with any of the many types of sprayers and granular applicators which are in wide use for the distribution of agricultural chemicals over soil or standing vegetation. In general, the compositions are formulated in the manners usual in agricultural chemistry.

Very often, the compounds are formulated as concentrated compositions which are applied either to the soil or the foliage in the form of water dispersions or emulsions containing in the range of from about 0.1 percent to about 5 percent of the compound. Water-dispersible or emulsifiable compositions are either solids usually known as wettable powders, or liquids usually known as emulsifiable concentrates. Wettable powders comprise as intimate, finely-divided mixture of the compound, an inert carrier, and surfactants. The concentration of the compound is usually from about 10 percent to about 90 percent. The inert carrier is usually chosen from among the attapulgite clays, the montmorillonite clays, the kaolin clays, the diatomaceous earths and the purified silicates. Effective surfactants, comprising from about 0.5 percent to about 10 percent of the wettable powder, are found among the sulfonated lignins, the condensed naphthalenesulfonates, the naphthalenesulfonates, the alkylbenzenesulfonates, the alkyl sulfates and nonionic surfactants such as ethylene oxide adducts of phenol.

Typical emulsifiable concentrates of the new compounds comprise a convenient concentration of the compound, such as from about 100 to about 500 g. per liter of liquid, dissolved in an inert carrier which is a mixture of water-immiscible solvent and emulsifiers. Useful organic solvents include the aromatics, especially the xylenes, and the petroleum fractions, especially the high-boiling naphthalenic and olefinic portions of petroleum. Many other organic solvents may also be used such as the terpenic solvents, and the complex alcohols such as 2-ethoxyethanol. Suitable emulsifiers for emulsifiable concentrates are chosen from the same types of surfactants used for wettable powders.

When a compound is to be applied to the soil, as for a preemergence application of the compound, it is convenient to use a granular formulation. Such a formulation typically comprises the compound dispersed on a granular inert carrier such as coarsely ground clay. The particle size of granules usually ranges from about 0.1 to about 3 mm. The usual formulation process for granules comprises dissolving the compound in an inexpensive solvent and applying the solution to the carrier in an appropriate solids mixer. Somewhat less economically, the compound may be dispersed in a dough composed of damp clay or other inert carrier, which is then dried and coarsely ground to produce the desired granular product.

It has become customary in agricultural chemistry to apply two or even more agricultural chemicals simultaneously in order to control weeds of many different types, or weeds and other pests, with a single application of chemicals. The compounds of this invention lend themselves well to combination with other agricultural chemicals and may usefully be combined with insecticides, fungicides, nematocides and other herbicides as may be desirable.

We claim:
1. A compound of the formula

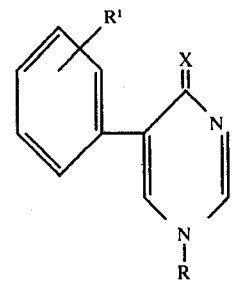

wherein
R represents $C_1$–$C_3$ alkyl;
$R^1$ represents bromo, chloro or trifluoromethyl;
X represents oxygen or sulfur.
2. The compound of claim 1 which is 1-methyl-5-($\alpha,\alpha,\alpha$-trifluoro-m-tolyl)-4(1H)-pyrimidinone.
3. The compound of claim 1 which is 1-methyl-5-(3-chlorophenyl)-4(1H)-pyrimidinone.
4. The compound of claim 1 which is 1-ethyl-5-($\alpha,\alpha,\alpha$-trifluoro-m-tolyl)-4(1H)-pyrimidinone.
5. The compound of claim 1 which is 1-methyl-5-(3-bromophenyl)-4(1H)-pyrimidinone.
6. The compound of claim 1 which is 1-methyl-5-($\alpha,\alpha,\alpha$-trifluoro-m-tolyl)-4(1H)-pyrimidinethione.

* * * * *